United States Patent
Sauer

[19]

[11] Patent Number: 6,121,510
[45] Date of Patent: Sep. 19, 2000

[54] ABSORBENT ARTICLE HAVING IMPROVED CONTAINMENT FLAPS

[75] Inventor: Barbara Oakley Sauer, Fremont, Wis.

[73] Assignee: Kimberly-Clark Worldwide, Inc., Neenah, Wis.

[21] Appl. No.: 08/984,347

[22] Filed: Dec. 3, 1997

[51] Int. Cl.$^7$ ................................................. A61F 13/15
[52] U.S. Cl. ..................... 604/378; 604/358; 604/375; 604/385.01; 604/385.101; 604/367; 604/370; 604/385.24
[58] Field of Search ................ 604/370, 385.2, 604/385.1, 219, 358, 375, 385.01, 385.101, 367, 378, 385.24; 428/219

[56] References Cited

U.S. PATENT DOCUMENTS

| | | | |
|---|---|---|---|
| Re. 33,106 | 11/1989 | Beckestrom | 604/385.2 |
| 4,490,148 | 12/1984 | Beckestrom | 604/385 |
| 4,662,877 | 5/1987 | Williams | 604/385 A |
| 4,681,579 | 7/1987 | Toussant et al. | 604/385 R |
| 4,695,278 | 9/1987 | Lawson | 604/385 A |
| 4,704,116 | 11/1987 | Enloe | 604/385 A |
| 4,738,677 | 4/1988 | Foreman | 604/385 R |
| 4,743,246 | 5/1988 | Lawson | 604/385 A |
| 4,755,179 | 7/1988 | Shiba et al. | 604/370 |
| 4,795,454 | 1/1989 | Dragoo | 604/385.2 |
| 4,798,603 | 1/1989 | Meyer et al. | 604/378 |
| 4,808,177 | 2/1989 | DesMarais et al. | 604/385.1 |
| 4,808,178 | 2/1989 | Aziz et al. | 604/385.2 |
| 4,816,025 | 3/1989 | Foreman | 604/385.2 |
| 4,822,435 | 4/1989 | Igaue et al. | 156/164 |
| 4,834,740 | 5/1989 | Suzuki et al. | 604/385.2 |
| 4,846,823 | 7/1989 | Enloe | 604/385.2 |
| 4,883,482 | 11/1989 | Gandrez et al. | 604/385.2 |
| 4,892,536 | 1/1990 | DesMarais et al. | 604/385.2 |
| 4,900,384 | 2/1990 | Sanders et al. | 156/204 |
| 4,904,251 | 2/1990 | Igaue et al. | 604/385.2 |
| 4,909,803 | 3/1990 | Aziz et al. | 604/385.2 |
| 4,938,755 | 7/1990 | Foreman | 604/385.2 |
| 4,990,147 | 2/1991 | Freeland | 604/385.2 |
| 5,021,051 | 6/1991 | Hiuke | 604/385.2 |
| 5,026,364 | 6/1991 | Robertson | 604/385.1 |
| 5,032,120 | 7/1991 | Freeland et al. | 604/385.2 |
| 5,061,261 | 10/1991 | Suzuki et al. | 604/385.2 |
| 5,064,489 | 11/1991 | Ujimoto et al. | 156/164 |
| 5,085,654 | 2/1992 | Buell | 604/370 |
| 5,114,420 | 5/1992 | Igaue et al. | 604/385.2 |
| 5,167,653 | 12/1992 | Igaue et al. | 604/385.2 |
| 5,176,668 | 1/1993 | Bernardin | 604/368 |
| 5,176,672 | 1/1993 | Bruemmer et al. | 604/385.1 |
| 5,190,606 | 3/1993 | Merkatoris et al. | 156/164 |
| 5,192,606 | 3/1993 | Proxmire et al. | 428/284 |
| 5,207,662 | 5/1993 | James | 604/385.2 |

(List continued on next page.)

FOREIGN PATENT DOCUMENTS

| | | | |
|---|---|---|---|
| 0 626 160 A1 | 11/1994 | European Pat. Off. | A61F 13/15 |
| 2 561 078 A1 | 9/1985 | France | A41B 13/02 |
| 2 699 812 A1 | 7/1994 | France | A61F 13/46 |
| 3-218751 | 9/1991 | Japan | A41B 13/02 |
| 4-152947 | 5/1992 | Japan | A41B 13/02 |
| 2 280 593 | 2/1995 | United Kingdom | A61F 13/15 |
| 2 296 192 | 6/1996 | United Kingdom | A61F 13/15 |
| WO 93/02647 A1 | 2/1993 | WIPO | A61F 13/15 |

*Primary Examiner*—John G. Weiss
*Assistant Examiner*—Miley Craig Peppers, III
*Attorney, Agent, or Firm*—Jeffrey B. Curtin

[57] ABSTRACT

An absorbent article includes at least one containment flap which is configured to maintain a perpendicular, spaced relation away from the absorbent article in use to reduce the flow of body exudates from the article. The article further includes a dewatering layer located on an outer surface of the containment flap for absorbing at least a portion of any exudates which pass over said containment flap in use. The dewatering layer defines an absorbency of at least about 3 grams of saline solution per gram of material. The dewatering layer may further define a total absorbency of at least about 0.5 grams of saline solution and an incline absorbency of at least 1 milliliter.

25 Claims, 3 Drawing Sheets

U.S. PATENT DOCUMENTS

| | | | |
|---|---|---|---|
| 5,224,941 | 7/1993 | Simmons | 604/385.2 |
| 5,236,428 | 8/1993 | Zajaczkowski | 604/385.2 |
| 5,246,431 | 9/1993 | Minetola et al. | 604/385.2 |
| 5,246,432 | 9/1993 | Suzuki et al. | 604/385.2 |
| 5,269,775 | 12/1993 | Freeland et al. | 604/385.2 |
| 5,275,590 | 1/1994 | Huffman et al. | 604/385.2 |
| 5,292,316 | 3/1994 | Suzuki | 604/385.2 |
| 5,304,159 | 4/1994 | Tanji et al. | 604/385.2 |
| 5,304,160 | 4/1994 | Igaue et al. | 604/385.2 |
| 5,306,268 | 4/1994 | Enloe | 604/385.2 |
| 5,378,528 | 1/1995 | Makoui | 428/219 |
| 5,509,915 | 4/1996 | Hanson et al. | 604/378 |
| 5,662,637 | 9/1997 | Kitaoka et al. | 604/385.2 |
| 5,669,896 | 9/1997 | Kielpikowski | 604/385.2 |
| 5,674,213 | 10/1997 | Sauer | 604/385.1 |

ABSORBENT ARTICLE HAVING IMPROVED CONTAINMENT FLAPS

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which include containment flaps along their side or end edges to prevent leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have typically included elasticized waistbands and leg cuffs to help reduce the leakage of body exudates. Some conventional absorbent articles have also included elasticized containment or barrier flaps at the leg or waist sections of the article to further reduce leaks.

However, conventional absorbent articles which incorporate containment flaps at their leg and waist sections have not been completely satisfactory. For example, some conventional absorbent articles which incorporate such flaps have not provided a good seal between the distal edge of the flap and the wearer's skin. The poor seal between the flap and the skin of the wearer has undesirably resulted in leakage of body exudates and, in particular, runny fecal material. The exudates have passed over the distal edge of the flap and along the wearer's skin undesirably soiling the wearer's garments.

In an effort to solve such leakage problems, many conventional absorbent articles include elastic members along the distal edge of the flap to gather and shirr the distal edge of the flap to provide a closer fit to the wearer. The use of such elastics along the distal edge of the flaps has resulted in an improved seal between the distal edge of the flap and the wearer's skin. However, to provide such an improved seal, it is often required to attach such elastics at high levels of tension or elongation which can undesirably result in increased red marking and irritation of the wearer's skin.

As a result, conventional absorbent articles having containment flaps at their leg and waist sections have not been completely satisfactory. Accordingly, there remains a need for improved containment at the leg and waist sections of absorbent articles.

SUMMARY OF THE INVENTION

In response to the difficulties and problems discussed above, a new disposable absorbent article which has improved containment flaps has been discovered.

As used herein, the "absorbency" of a material refers to the absorbency value obtained when subjecting the material to the Absorbent Capacity Test set forth below in the Test Procedures section. As used herein, the term "saline solution" refers to a 0.9 weight percent solution of sodium chloride in distilled water.

In one aspect, the present invention relates to an absorbent article which comprises at least one containment flap which is configured to maintain a perpendicular, spaced relation away from the absorbent article in use to reduce the flow of body exudates from the article. The article further includes a dewatering layer located on an outer surface of the containment flap for absorbing at least a portion of any exudates which pass over the containment flap in use. In a specific aspect, the dewatering layer is smaller in size than the containment flap. The dewatering layer may also define an absorbency of at least about 3 grams of saline solution per gram of material and a total absorbency of at least about 0.5 grams of saline solution.

In another aspect, the present invention concerns an absorbent article having a front waist section, a rear waist section, an intermediate section which interconnects the front and rear waist sections, a pair of longitudinally opposed end edges, and a pair of laterally opposed side edges. The article includes an absorbent chassis, a pair of containment flaps which extend longitudinally along said side edges of the absorbent article and a dewatering layer on the outer surface of each of the containment flaps. The containment flaps include a proximal edge which is at least partially joined to the absorbent chassis and a distal edge opposite the proximal edge which remains unattached to the absorbent chassis in at least the intermediate section. The distal edge is configured to maintain a spaced relation away from the absorbent chassis in at least the intermediate section and a contacting relation with a wearer's body in use. The dewatering layer is located on the outer surface of each of the containment flaps for absorbing at least a portion of any exudates which pass between the distal edge and the wearer's body in use. In a specific aspect, the dewatering layer defines a length which is less than about 60 percent of a length of the containment flap. The dewatering layer may further define an absorbency of at least about 3 grams of saline solution per gram.

In still another aspect, the present invention relates to an absorbent article having a front waist section, a rear waist section, an intermediate section which interconnects the front and rear waist sections, a pair of longitudinally opposed end edges, and a pair of laterally opposed side edges. The article includes an absorbent chassis, a containment flap which extends laterally along one of the end edges of the absorbent article and a dewatering layer located on an outer surface of the containment flap. The containment flap includes a proximal edge which is at least partially joined to the absorbent chassis and a distal edge opposite the proximal edge which remains at least partially unattached to the absorbent chassis in between the side edges of the absorbent article. The distal edge is configured to maintain a spaced relation away from the absorbent chassis and a contacting relation with the wearer's body in use. The dewatering layer is located on an outer surface of each of the containment flaps for absorbing at least a portion of any exudates which pass between the distal edge and the wearer's body in use.

The various aspects of the present invention can advantageously provide an absorbent article having improved containment flaps. In particular, the present invention provides containment flaps for absorbent articles which include a dewatering material on the outer surface thereof. The dewatering material is configured to absorb any exudates which pass over the distal edge of the containment flap and between the distal edge and the wearer's skin. In particular, such dewatering material is configured to absorb any liquid exudates and at least a portion of the liquid content of any fecal exudates which may pass over the distal edge of the containment flap. Thus, such dewatering material may desorb the fecal exudates which will reduce if not stop any flow of such exudates from the article. As a result, the use of such a dewatering material on the outer surface of the containment flaps can result in reduced levels of leakage from the absorbent article.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
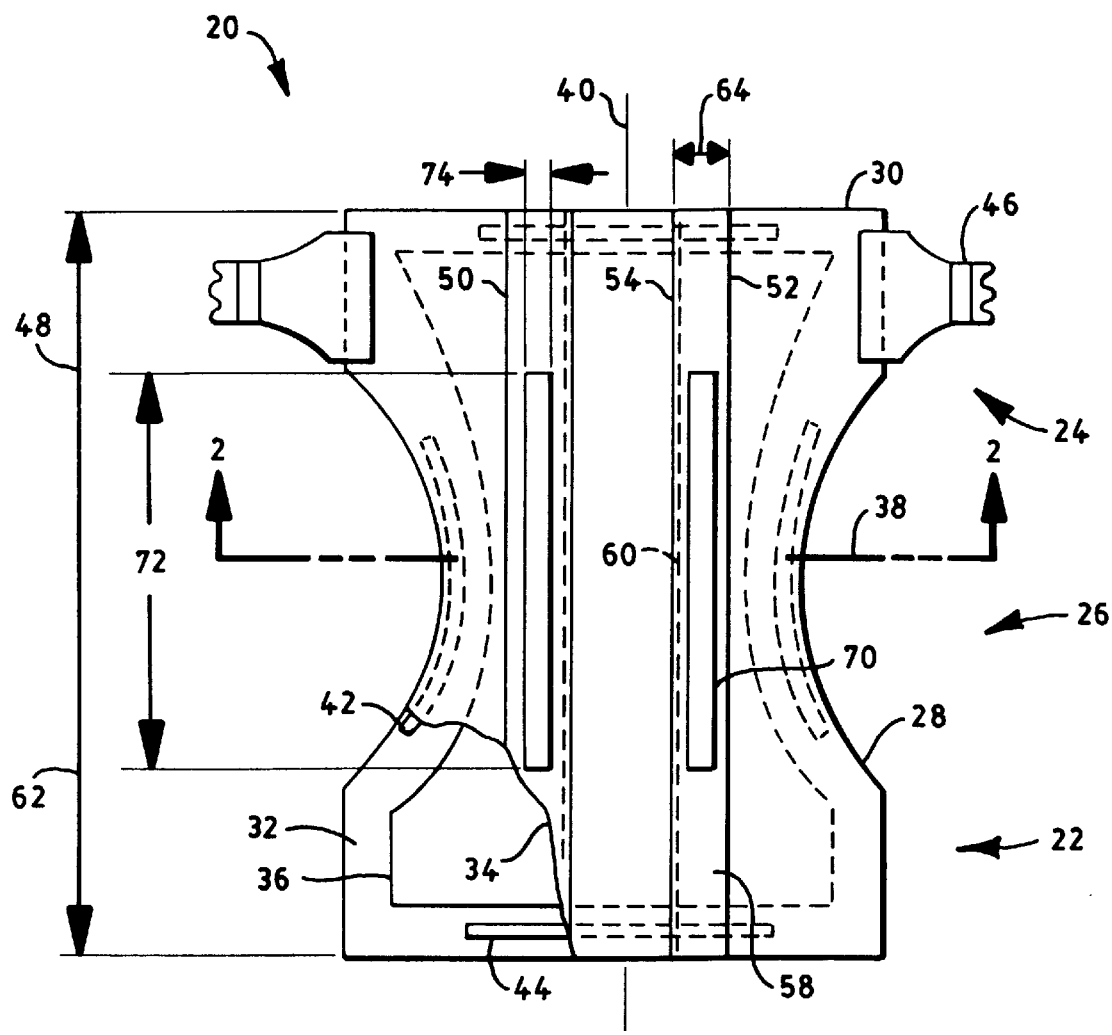
FIG. 1 representatively shows a partially cut away, top plan view of an absorbent article according to one embodiment of the invention.
Figure 5:
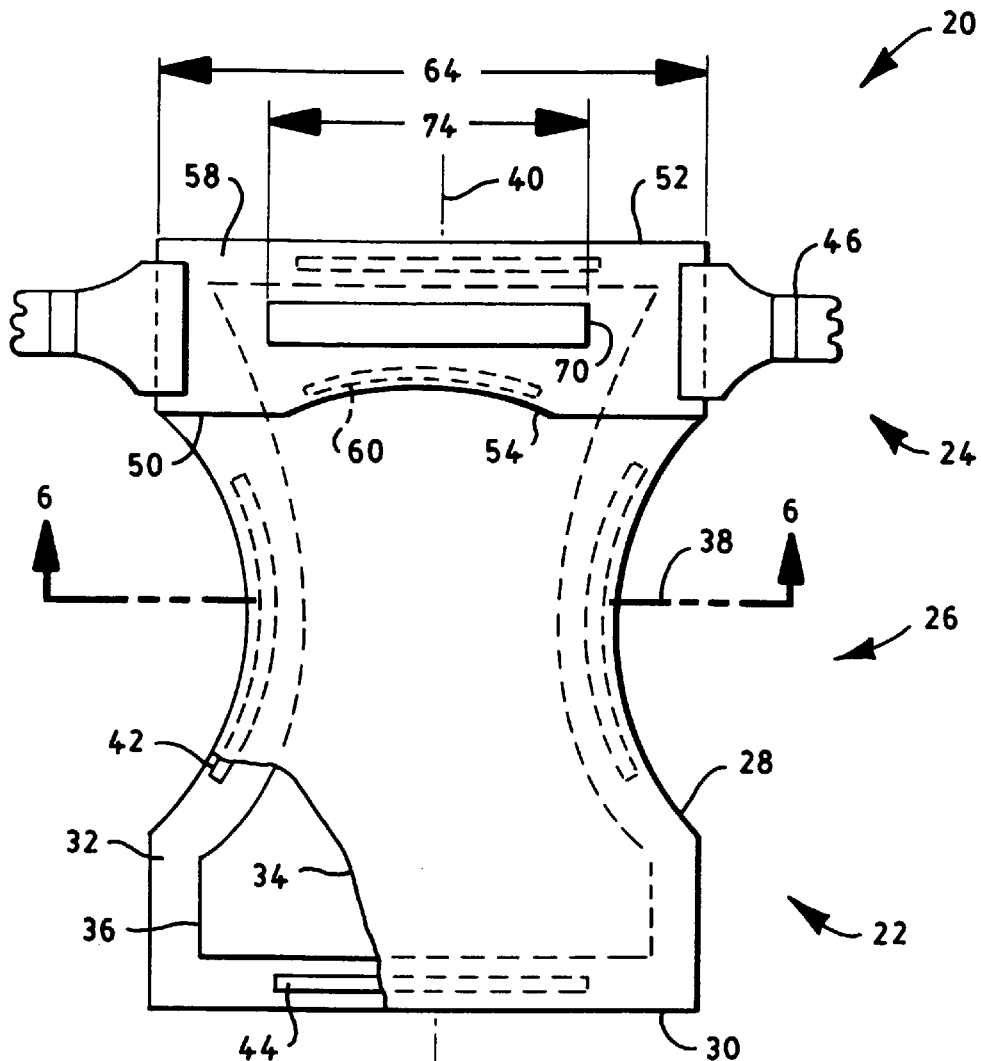
FIG. 5 representatively shows a partially cut away, top plan view of an absorbent article according to another embodiment of the invention.

With reference to FIGS. 1 and 5, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

Figure 2:
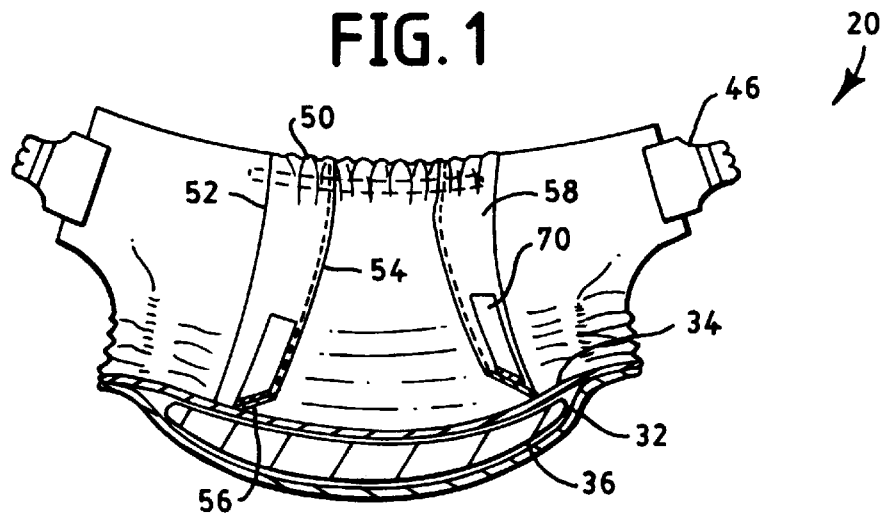
FIG. 2 representatively shows a sectional view of the absorbent article of FIG. 1 taken along line 2—2 wherein the elastic segments have been allowed to contract and gather the article.
Figure 6:
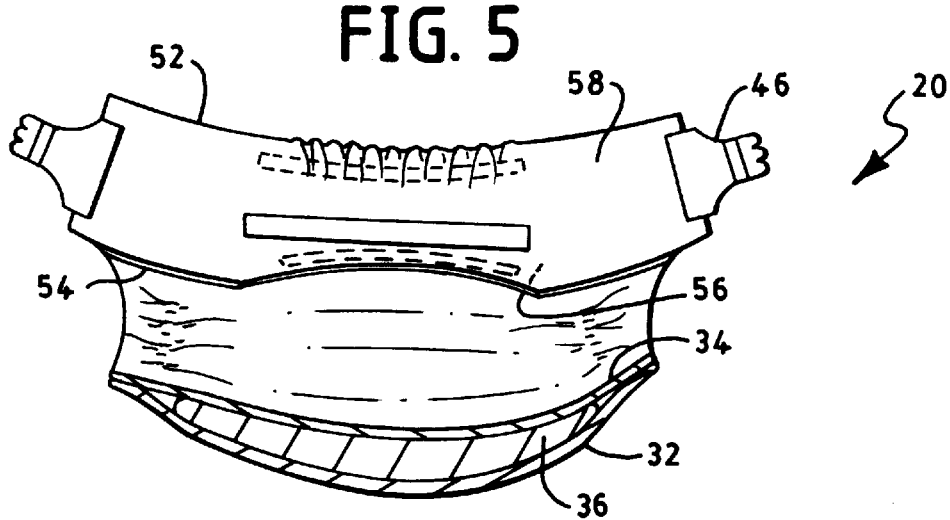
FIG. 6 representatively shows a sectional view of the absorbent article of FIG. 5 taken along line 6—6 wherein the elastic segments have been allowed to contract and gather the article.

FIGS. 1 and 5 are representative plan views of two variations of the diaper 20 of the present invention in a flat, uncontracted state. Portions of the structure are partially cut away to more clearly show the interior construction of the diaper 20, and the surface of the diaper which contacts the wearer is facing the viewer. FIGS. 2 and 6 representatively shows a sectional view of the diaper 20 of FIGS. 1 and 5 taken along lines 2—2 and 6—6, respectively, wherein the elastics have been allowed to contract and gather the diaper 20. The diaper 20 includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The combination of the backsheet 32, the topsheet 34 and the absorbent body 36 defines an absorbent chassis. The diaper 20 also defines a lateral centerline 38, a longitudinal centerline 40 and a longitudinal length 48 measured along the longitudinal centerline 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins and end margins of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins and end margins of the diaper may be elasticized with suitable elastic members, such as leg elastic members 42 and waist elastic members 44. For example, the leg elastic members 42 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 44 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 42 and 44 are secured to the diaper 20 in an elastically contractible condition so that in a normal under strain configuration, the elastic members effectively contract against the diaper 20. For example, the elastic members 42 and 44 may be elongated and secured to the diaper 20 while the diaper is in an uncontracted condition. In FIGS. 1 and 5, the elastic members 42 and 44 are illustrated in their uncontracted, stretched condition for the purpose of clarity. Alternatively, the diaper 20 may include a pair of separate, elasticized and gathered leg gussets (not shown) which are attached to the diaper along the side margins in at least the intermediate section 26 of the diaper 20 to provide elasticized leg cuffs. Such leg gussets may be configured to extend beyond and bridge across the respective concave portion of the side margins of the diaper 20.

The diaper 20, as representatively illustrated in FIGS. 1 and 5, may further include a pair of fasteners 46 which are employed to secure the diaper 20 about the waist of a wearer. Suitable fasteners 46 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral centerline 38 of the diaper 20.

The diaper 20 representatively illustrated in FIGS. 1 and 5 further includes at least one elasticized, containment flap 50 which is configured to maintain an upright, perpendicular arrangement to serve as an additional barrier to the flow of exudates. For example, in the embodiment representatively illustrated in FIGS. 1 and 2, the diaper 20 may include a pair of longitudinally extending containment flaps 50 along the side edges 28 of the diaper 20. In such a configuration, the containment flaps 50 are configured to maintain an upright, perpendicular arrangement in at least the intermediate section 26 of the diaper 20 to serve as an additional barrier to the lateral flow of body exudates. As representatively illustrated in FIGS. 5 and 6, the diaper 20 may also or otherwise include at least one containment flap 50 located in a waist section of the diaper 20 to prevent the longitudinal flow of exudates out of the diaper 20. For example, the diaper 20 may include a containment flap 50 located along the end edge 30 in the rear waist section 24 of the diaper 20.

The diaper 20 may further include a surge management layer (not shown) positioned between the topsheet 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent articles of the present invention.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 42 and 44 and the fasteners 46, may be assembled into the diaper 20 article by employing the above-identified attachment mechanisms.

The backsheet 32 of the diaper 20, as representatively illustrated in FIGS. 1, 2, 5 and 6, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIGS. 1, 2, 5 and 6, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearer's skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIGS. 1, 2, 5 and 6, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The diaper 20, as representatively illustrated in FIGS. 1, 2, 5 and 6, further includes at least one containment flap 50 located along a side edge 28 or end edge 30 of the diaper 20 to prevent the flow of exudates out of the diaper. For example, the diaper 20 illustrated in FIGS. 1 and 2 includes a pair of longitudinally extending containment flaps 50 located along the side margins of the diaper 20. The containment flaps 50 are configured to provide a barrier to the lateral flow of body exudates in at least the intermediate section 26 of the diaper 20. Thus, such containment flaps may reduce leakage from the leg regions of the diaper 20. Whereas, the diaper 20 illustrated in FIGS. 5 and 6 includes a laterally extending containment flap 50 along the end margin in the rear waist section 24 of the diaper 20. Such a containment flap 50 is configured to provide a barrier to the longitudinal flow of body exudates in the rear waist section 24 of the diaper 20.

The diaper 20 of the different aspects of the present invention may include any combination of containment flaps. For example, the diaper 20 may include containment flaps along both side margins and one or both end margins of the diaper 20 for improved containment. The diaper 20 may otherwise include a single containment flap 50 which is similar in shape and size to the absorbent chassis but which has an opening therein to allow exudates to pass into the interior of the diaper 20 for absorption by the absorbent body 36. In alternative embodiments, the diaper 20 may include multiple containment flaps 50 along each side edge 28 or end edge 30 of the diaper 20 which may define troughs or channels in between each containment flap 50.

Figure 3:
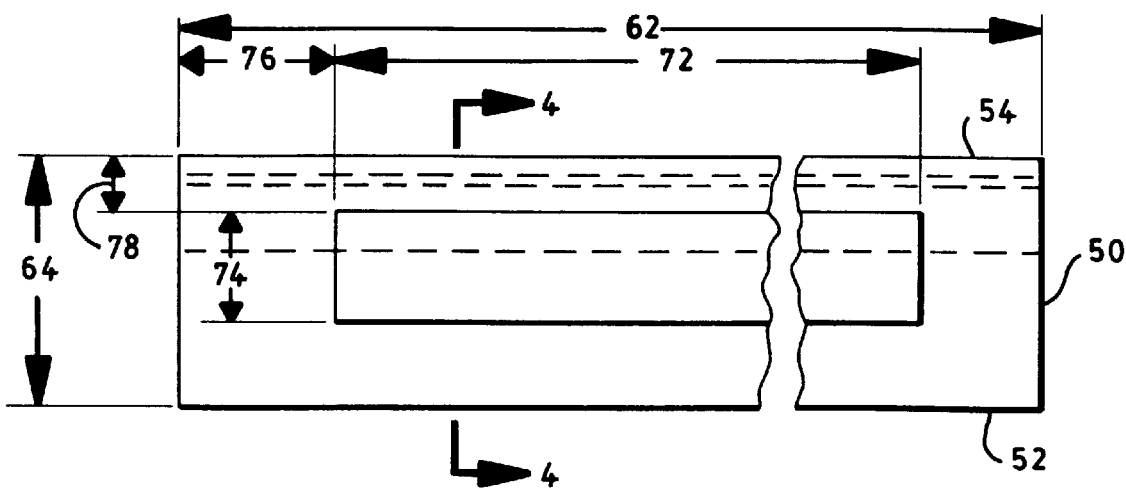
FIG. 3 representatively shows a side elevational view of one of the containment flaps of the absorbent article of FIG. 1.
Figure 4:
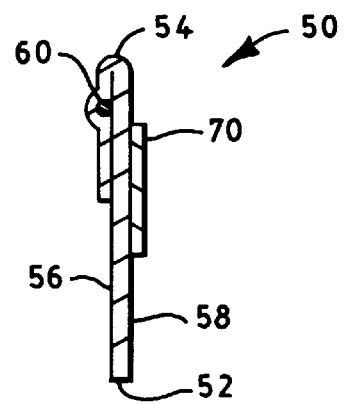
FIG. 4 representatively shows a sectional view of the containment flap of FIG. 3 taken along line 4—4.

FIG. 3 illustrates a representative example of one of the containment flaps 50 of the diaper illustrated in FIGS. 1 and 2 and FIG. 4 illustrates a cross-sectional view of the containment flap 50 of FIG. 3 taken along lines 4—4. In the different aspects of the present invention, each of the containment flaps 50 defines a proximal edge 52, a distal edge 54, an inner surface 56 and an outer surface 58. The inner surface 56 of each containment flap is the surface of the flap which is configured to face inward towards the lateral or longitudinal centerline 38 or 40 of the diaper 20. While the outer surface 58 of each containment flap 50 is opposite the inner surface 56 and is configured to face outward away from the lateral or longitudinal centerline 38 or 40 of the diaper 20. Each containment flap 50 further defines a length 62 and a width 64.

The containment flaps 50 may be integral with or formed separate from the absorbent chassis and joined thereto. Methods of joining the containment flaps 50 to the absorbent chassis are known to those skilled in the art. Suitable methods include heat sealing, sonic bonding, adhesive bonding, and the like. It is generally preferred that the containment flaps 50 be formed separate and attached to the absorbent chassis. For example, in the embodiment illustrated in FIGS. 1 and 2, it is desirable that the containment flaps 50 be attached to the absorbent chassis close to a lateral edge of the absorbent core 36 in at least the intermediate section 26 of the diaper 20. In the embodiment illustrated in FIGS. 5 and 6, it is desirable that the containment flap 50 be attached adjacent the end edge 30 of the diaper 20.

Alternatively, the containment flaps 50 may be integrally formed from the backsheet 32 or topsheet 34 of the diaper 20. For example, the topsheet 34 may extend from the side edges 28 of the diaper 20 to the absorbent body 36 where the topsheet 34 can extend upwardly and be folded over upon itself to form the containment flaps 50 illustrated in FIGS. 1 and 2. Alternatively, the topsheet 34 may extend beyond the end edge 30 of the diaper 20 to form the containment flap 50 illustrated in FIGS. 5 and 6.

A wide range of materials are suitable for use as the containment flaps 50 as representatively illustrated in FIGS. 1, 2, 5 and 6. For example, the containment flaps 50 can include a nonwoven material such as a spunbond, meltblown, spun laced or carded polymeric material, a film material such as a polyolefin or polyurethane film, a foam material or combinations thereof. The containment flaps 50 may also include materials described above as being suitable for the backsheet 32 or topsheet 34 of the diaper 20. In a specific embodiment, the containment flaps 50 may be formed from a nonwoven material such as a spunbond or meltblown polyethylene or polypropylene material.

Many nonwoven materials are formed from hydrophobic materials. Such hydrophobic materials result in nonwovens which are somewhat resistant to the flow of liquids. If it is desired that the containment flaps 50 be generally liquid pervious, such nonwoven materials may be treated with a surfactant to render them generally hydrophilic. Alternatively, if it is desired that the containment flaps 50 be liquid impervious, the containment flaps 50 can include a liquid-impervious film such as a polyolefin film. In a specific embodiment, the containment flaps 50 comprise a spunbond/meltblown/spunbond laminate material having a basis weight of about 30 grams per square meter. Methods of making such materials are known to those skilled in the art.

At least a portion of the proximal edge 52 of each containment flap 50 is joined to the absorbent chassis to maintain a seal between the containment flap and the absorbent chassis. Desirably, the proximal edge 52 is joined to the absorbent chassis along the entire length 62 or width 64 of the containment flap 50 for improved containment of body exudates and reduced leakage. For example, as representatively illustrated in FIGS. 1 and 2, the proximal edge 52 of each containment flap 50 may be joined to the topsheet 34 of the diaper 20 at least in the intermediate section 26 of the diaper 20 and desirably along the entire length of the containment flap 50. If the containment flap 50 is located in a waist region as representatively illustrated in FIGS. 5 and 6, at least a portion of the proximal edge 52 of each containment flap 50 is joined to the topsheet 34 of the diaper 20 adjacent the end edge 30 of the diaper 20 and desirably along the entire width of the containment flap 50.

At least a portion of the distal edge 54 of each containment flap 50 is not attached to the absorbent chassis such that the containment flap 50 provides a barrier to the lateral flow of body exudates. For example, as representatively illustrated in FIGS. 1 and 2, the distal edge 54 of each containment flap 50 may be joined to the topsheet 34 in at least a portion of the front waist section 22 and rear waist section 24 of the diaper 20 and remain unjoined to the topsheet 34 in at least a portion of the intermediate section 26 of the diaper 20. In such a configuration, the distal edge 54 of each containment flap 50 is configured to position itself in a spaced relation away from the absorbent chassis toward a generally upright and approximately perpendicular configuration in at least the intermediate section 26 of the diaper 20. Alternatively, in the embodiment illustrated in FIGS. 5 and 6, the distal edge 54 of each containment flap 50 may be joined to the topsheet 34 adjacent the side edges 28 of the diaper 20 and remain unjoined to the topsheet 34 in at least a portion of the diaper 20 between the side edges 28. In such a configuration, the distal edge 54 of each containment flap 50 is configured to position itself in a spaced relation away from the absorbent chassis toward a generally upright and approximately perpendicular configuration in between the side edges 28 of the diaper 20.

To achieve such a spaced away, upright configuration, each containment flap 50 includes at least one elastic member 60 along at least a portion of the distal edge 54 of the containment flap 50 and, more desirably, along the entire distal edge 54 of the containment flap 50. The elastic member 60 is secured to the containment flap 50 in an elastically contractible condition so that in a normal under strain configuration, the elastic member 60 effectively contracts against the containment flap 50. For example, the elastic member 60 may be elongated and secured to the containment flap 50 while the flap is in an uncontracted condition. In FIGS. 1 and 5, the elastic members 60 are illustrated in their uncontracted, stretched condition for the purpose of clarity. As a result, the distal edge 54 of each containment flap 50 tends to contract or gather and position itself in a spaced relation away from the absorbent chassis and, in particular, the topsheet 34 of the diaper 20 toward a generally upright and approximately perpendicular configuration.

Each containment flap 50 may include any number of individual elastic members which provide the desired spaced away configuration. In the illustrated embodiments, each containment flap 50 includes an elastic member 60 which is in the form of a single elastomeric strand. Alternatively, each containment flap 50 may include from about 2 to about 10 elastomeric strands. Multiple elastomeric strands may be configured in a laterally spaced, generally parallel arrangement. Suitably, the elastic member 60 is configured parallel to the distal edge 54 of each containment flap 50 and is located within about 0.5 centimeters of the distal edge 54.

The elastic member 60 suitably comprises any elastomeric material capable of being elongated at least about 50 percent, desirably about 350 percent, and capable of recovering to within at least about 250 percent, and desirably about 150 percent of its original length after being elongated about 300 percent. In one specific embodiment, the elastic member 60 can, for example, be composed of a spandex elastomeric strand such as, for example, a 470 decitex Lycra thread commercially available from E. I. DuPont de Nemours and Co. Alternatively, the elastic member 60 can be composed of a thermoplastic elastomer or a natural or synthetic rubber commercially available from J.P.S. Elastomerics Corp. The elastic member 60 can also be composed of a heat activatable elastic material such as PEBAX, commercially available from Atochem, Inc., which can be activated with heat treatment after the elastic member 60 is secured to the containment flap 50. The elastic member can be attached to the containment flap 50 by any method known to those skilled in the art such as thermal bonding, adhesive bonding, ultrasonic bonding or the like.

The length 62 and width 64 of each containment flap 50 can vary depending on the type and size of the absorbent article to which it will be attached and the orientation of the containment flap 50 on the diaper 20. In a specific embodiment wherein the containment flaps 50 are disposed along the side edges 28 of the diaper 20 as illustrated in FIGS. 1 and 2, each containment flap 50 has an overall width 64 of at least about 1 centimeter and desirably from about 2 to about 3 centimeters and an overall length 62 of at least about 30 percent and desirably at least about 50 percent of the entire length 48 of the diaper 20. In a particular embodiment, the containment flap 50 will extend substantially the entire length 48 of the diaper for improved containment.

In an alternative embodiment wherein the containment flap 50 is disposed along the end edge 30 of the diaper 20 as illustrated in FIGS. 5 and 6, each containment flap 50 has an overall length in the longitudinal direction of at least about 2 centimeters and desirably from about 5 to about 10 centimeters and an overall width 64 in the lateral direction of at least about 30 percent and desirably at least about 50 percent of the entire width of the diaper 20. In a particular embodiment, the containment flap 50 will extend in the lateral direction substantially the entire width of the diaper for improved containment.

The diaper 20 of the different aspects of the present invention, as representatively illustrated in FIGS. 1–6, further includes a layer of dewatering material 70 on the outer surface 58 of at least one of the containment flaps 50. The dewatering material 70 is configured to absorb at least a portion of any exudates which pass over the containment flap 50 between the distal edge 54 of the containment flap 50 and the wearer's body. In particular, it is desirable that the dewatering material 70 absorb at least a portion of the liquid component of any fecal exudates or urine which pass over the containment flap 50 to inhibit the flow of such exudates out of the diaper 20 and into contact with the wearer's garments.

The dewatering material 70 may have any suitable shape and size which provide the desired absorption of the liquid exudates passing over the containment flap 50 to assist in preventing leakage. For example, the dewatering material 70, as representatively illustrated in FIGS. 1–6, can extend substantially along the entire length 62 and width 64 of the containment flap 50. Alternatively, the dewatering material 70 may extend along a portion of the length 62 and width 64 of the containment flap 50. For example, the dewatering material 70 may define a length 72 which extends from about 25 to about 75 percent of the length 62 of the containment flap 50 and a width 74 which extends from about 25 to about 75 percent of the width 64 of the containment flap 50. Desirably, the dewatering material 70 defines a length 72 and width 74 which are less than about 75 percent of the length 62 and width 64 of the containment flap 50 respectively for improved performance and cost effectiveness.

When the containment flaps 50 are positioned along the side edges 28 of the diaper 20 as representatively illustrated in FIGS. 1 and 2, it is desirably that the dewatering material 70 be located at least in the intermediate section 26 of the diaper 20 and spaced away from the distal edge 54 of the containment flap 50. For example, as representatively illustrated in FIG. 3, the dewatering material 70 may be spaced inwardly from each end edge of the containment flap a distance 76 of at from about 12.5 to about 37.5 percent of a length of the containment flap 50. The dewatering material 70 also may be spaced away from the distal edge 54 of the containment flap 50 a distance 78 of at least about 0.5 centimeters for improved performance. When the containment flaps 50 are positioned along the end edges 30 of the diaper 20 as representatively illustrated in FIGS. 5 and 6, it is desirably that the dewatering material 70 be located at least in the central portion of the diaper 20 near the longitudinal centerline 40 of the diaper 20. In a particular embodiment, the dewatering material 70 may be located such that it extends longitudinally to the distal edge 54 of the containment flap 50 and not over the waist elastic 44 of the diaper 20 for improved performance. In such configurations, the dewatering material 70 is less likely to be in contact with the skin of the wearer for improved consumer acceptance since the dewatering material may have an undesirable wet feel to it.

The dewatering material 70 is typically formed from a separate piece of material which is joined to the outer surface 58 of the containment flap 50. Methods of joining the dewatering material 70 to the containment flaps 50 are known to those skilled in the art. Suitable methods include heat sealing, sonic bonding, adhesive bonding, and the like.

To effectively inhibit the flow of exudates which pass over the containment flap 50, the dewatering material 70 defines an absorbency which is at least about 3 grams of saline solution per gram of material and desirably at least about 6 grams of saline solution per gram of material. The dewatering material 70 also defines a basis weight of at least about 30 grams per square meter and desirably at least about 50 grams per square meter such that it is capable of absorbing sufficient liquid exudates to reduce the flow of exudates out of the diaper 20. To effectively inhibit the flow of exudates along the containment flap 50, the dewatering material 70 further defines a total absorbency of at least about 0.5 grams of saline solution and desirably at least about 1 gram of saline solution.

Another property of the dewatering material 70 which indicates the ability of the dewatering material 70 to uptake any flow of exudates which pass over the containment flap 50 is the incline absorbency. As used herein, the "incline absorbency" of a material refers to the value obtained when subjecting the material to the Incline Plane Test set forth below in the Test Procedures section. In general, a strip of the material is placed on an incline plane which is at an angle of 30 degrees relative to the horizontal. One milliliter aliquots of saline solution are then dispensed about 2.54 centimeters above the material and allowed to run down onto the material. The amount of saline solution dispensed before run-off from the material and failure is then measured. In a particular embodiment, the dewatering material 70 of the different aspects of the present invention defines an incline absorbency of at least 1 milliliter and desirably at least 2 milliliters for improved performance.

A wide range of materials are suitable for use as the dewatering material 70 as representatively illustrated in FIGS. 1–6. For example, the dewatering material 70 can include a nonwoven material such as a spunbond, meltblown, spun laced or carded web of natural fibers, synthetic fibers, polymeric fibers and the like or combinations thereof which has the desired properties set forth above. Alternatively, the dewatering material 70 may include a foam material having the desired properties. Desirably, the dewatering material 70 includes hydrophillic fibers such as cellulose or rayon fibers for improved absorbency and performance. However, many nonwoven materials are formed from hydrophobic materials. Such hydrophobic materials typically are resistant to the flow of liquids and do not exhibit the desired properties recited above. Accordingly, if it is desired to use such nonwoven materials, they may be treated with a surfactant to render them generally hydrophilic. The fibers may also be oriented in one direction such that the dewatering material 70 has improved fluid wicking in that direction. For example, the dewatering material 70 on the containment flaps illustrated in FIGS. 1 and 2 desirably contains fibers which are oriented in the longitudinal for improved wicking.

In a specific embodiment, the dewatering material 70 may be formed from a nonwoven material such as a bonded carded web material which includes natural fibers. One such material is a bonded carded web material commercially available from E. I. DuPont de Nemours Co. a business having offices located in Delaware under the trade designation SONTARA 8423. Such material includes about 70 weight percent rayon fibers and about 30 weight percent polyester fibers for improved performance. Such a material may further define a basis weight of about 78 grams per square meter and an absorbency of about 8 grams of saline solution per gram of material. Alternatively, the dewatering material 70 may include an uncreped through air dried material comprising cellulosic fibers as described in commonly assigned copending U.S. patent application Ser. No. 08/614,420 filed Mar. 8, 1996, in the name of Chen et al., the disclosure of which is hereby incorporated by reference.

In an alternative embodiment, the layer of dewatering material 70 of the diaper 20 of the present invention may be located on the bodyfacing surface of the diaper 20 between the proximal edge 52 of the containment flaps 50 and the side edges 28 or end edges 30 of the of the diaper 20. In such a configuration, the dewatering material 70 is configured to absorb at least a portion of any exudates which pass over the containment flap 50 between the distal edge 54 of the containment flap 50 and the wearer's body.

The following Examples are presented to provide a more detailed understanding of the invention. The Examples are intended to be representative, and are not intended to limit the scope of the invention.

EXAMPLES

Test Procedures
Absorbent Capacity Test

The absorbent capacity test measures the amount of fluid which is retained in a sample of material after the sample is loaded with an amount of fluid and an external pressure is applied.

Equipment & Materials
1. Saline solution; 0.9 weight percent solution of sodium chloride in distilled water.
2. Saturation Tub to hold the sample to be tested.
3. Room with standard-condition atmosphere; Temperature= 23+1° C. (73.4+1.8° F.) and Relative Humidity=50+2%.

Specimen Preparation
1. Cut the samples to 2.54×15.24 centimeters.
2. Weigh each sample to the nearest 0.1 gram and record the weight on the data sheet.

Testing Procedure
1. Fill the Saturation Tub with the saline solution to a minimum depth of 2 inches (51 millimeters).
2. Submerge the material samples in the saline solution.
3. Saturate the samples for 30 seconds.
4. Remove the samples from the saline solution and allow the samples to drip for one minute.
5. Weigh the samples to the nearest 0.1 gram.
6. The Absorbency of each sample is then calculated thus:
Absorbency=(Wet weight−Dry weight)/Dry weight Incline Plane Test
1. The incline plane test measures the ability of a sample of material to rapidly uptake fluid which is allowed to run over the material.

Equipment & Materials
1. Saline solution; 0.9 weight percent solution of sodium chloride in distilled water.
2. Lexan incline plane set at 30 degrees relative to the horizontal.
3. Room with standard-condition atmosphere; Temperature= 23+1° C. (73.4+1.8° F.) and Relative Humidity=50+2%.
4. Samples of material cut to 2.54×15.24 centimeters with the 15.24 centimeter dimension corresponding to the length of the material as it is to be used in the product.

Testing Procedure
1. Anchor the material sample to the incline plane using standard double sided adhesive tape such that the 15.24 centimeter dimension of the material extends down the incline plane.
2. Dispense 1 milliliter aliquots of saline solution at a distance of about 2.54 centimeters above the material sample with 15 seconds between each aliquot until saline solution runs off the material.
3. The Incline Absorbency of each sample is the amount of saline solution added until failure.

Example

A bonded carded web material suitable for use as the dewatering material of the different aspects of the present invention was tested. The material was commercially available from E. I. DuPont de Nemours Co. under the trade designation SONTARA 8423. The test material included about 70 weight percent rayon fibers and about 30 weight percent polyester fibers and defined a basis weight of about 78 grams per square meter. The test material was subjected to the Absorbent Capacity Test and defined an absorbency of 7.1 grams of saline solution per gram of material. The test material was also subjected to the Incline Plane Test and defined an incline absorbency of 3 milliliters.

Comparative Example 1

Containment flaps from HUGGIES® Ultratrim diapers commercially available from Kimberly-Clark Corporation were obtained. The containment flaps included a spunbond/meltblown/spunbond laminate material having a basis weight of about 28 grams per square meter. The spunbond layers included polypropylene fibers, and the meltblown layer included meltblown polypropylene fibers. A test sample of the containment flap material was subjected to the Absorbent Capacity Test and defined an absorbency of 2.5 grams of saline solution per gram of material. In the Absorbent Capacity Test, the majority of the saline solution which remained on the test sample was in the form of droplets on the outer surface of the material. These droplets were included in the results. Thus, the actual amount of saline absorbed into the test sample was less than indicated by the Absorbent Capacity Test. The containment flap material was also subjected to the Incline Plane Test and defined an incline absorbency of 1 milliliter.

The Example and Comparative Example representatively illustrate the improved absorbency properties of the dewatering material of the different aspects of the present invention when compared to materials being used for containment flaps on conventional diapers. As discussed above, the use of a dewatering material with such improved absorbency can effectively reduce leakage from the side and end edges of the diaper by absorbing liquids which pass between the containment flaps and the body of the wearer in use.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. An absorbent article which comprises a backsheet layer, a liquid permeable topsheet layer which is connected in superposed relation to said backsheet layer, an absorbent body which is located between said topsheet layer and said backsheet layer, at least one containment flap which is configured to maintain a perpendicular, spaced relation away from said absorbent article in use to reduce the flow of body exudates from said article and a dewatering layer formed from a material separate from said containment flap and also joined on an outer surface of said containment flap for absorbing at least a portion of any exudates which pass over said containment flap in use.

2. An absorbent article according to claim 1 wherein said containment flap includes a material which is hydrophobic.

3. An absorbent article according to claim 1 wherein said dewatering layer defines a length which is less than a length of said containment flap.

4. An absorbent article according to claim 1 wherein said dewatering layer defines a length which is less than about 75 percent of a length of said containment flap.

5. An absorbent article according to claim 1 wherein said dewatering layer defines a width which is less than a width of said containment flap.

6. An absorbent article according to claim 1 wherein said dewatering layer defines a width which is less than about 75 percent of a width of said containment flap.

7. An absorbent article according to claim 1 wherein said dewatering layer comprises a hydrophilic material.

8. An absorbent article according to claim 1 wherein said dewatering layer defines an absorbency of at least about 3 grams of saline solution per gram.

9. An absorbent article according to claim 1 wherein said dewatering layer defines a basis weight of at least about 30 grams per square meter.

10. An absorbent article according to claim 1 wherein said dewatering layer comprises natural fibers.

11. An absorbent article according to claim 1 wherein said dewatering layer comprises a combination of rayon fibers and polyester fibers.

12. An absorbent article having a front waist section, a rear waist section, an intermediate section which interconnects said front and rear waist sections, a pair of longitudinally opposed end edges, and a pair of laterally opposed side edges, said article comprising:
  a) an absorbent chassis which includes a backsheet layer, a liquid permeable topsheet layer which is connected in superposed relation to said backsheet layer, and an absorbent body which is located between said topsheet layer and said backsheet layer;
  b) a pair of containment flaps which extend longitudinally along said side edges of said absorbent article and which include a proximal edge which is at least partially joined to said absorbent chassis and a distal edge opposite said proximal edge which remains unattached to said absorbent chassis in at least said intermediate section and which is configured to maintain a spaced relation away from said absorbent chassis in at least said intermediate section and a contacting relation with a wearer's body in use; and
  c) a dewatering layer formed from a material separate from said containment flap and also joined on an outer surface of each of said containment flaps for absorbing at least a portion of any exudates which pass between said distal edge and said wearer's body in use.

13. An absorbent article according to claim 12 wherein said proximal edge of each of said containment flaps is attached to said topsheet layer of said absorbent chassis.

14. An absorbent article according to claim 12 wherein said dewatering layer defines a length which is less than about 75 percent of a length of said containment flap.

15. An absorbent article according to claim 12 wherein said dewatering layer defines a width which is less than about 75 percent of a width of said containment flap.

16. An absorbent article according to claim 12 wherein said dewatering layer defines an absorbency of at least about 3 grams of saline solution per gram.

17. An absorbent article according to claim 12 wherein said dewatering layer defines a basis weight of at least about 30 grams per square meter.

18. An absorbent article according to claim 12 wherein said dewatering layer comprises a combination of rayon fibers and polyester fibers.

19. An absorbent article according to claim 12 wherein said dewatering layer comprises a bonded carded web of natural fibers.

20. An absorbent article having a front waist section, a rear waist section, an intermediate section which interconnects said front and rear waist sections, a pair of longitudinally opposed end edges, and a pair of laterally opposed side edges, said article comprising:
  a) an absorbent chassis which includes a backsheet layer, a liquid permeable topsheet layer which is connected in superposed relation to said backsheet layer, and an absorbent body which is located between said topsheet layer and said backsheet layer;
  b) a containment flap which extends laterally along one of said end edges of said absorbent article and which includes a proximal edge which is at least partially joined to said absorbent chassis and a distal edge opposite said proximal edge which remains at least partially unattached to said absorbent chassis in between said side edges of said absorbent article and which is configured to maintain a spaced relation away from said absorbent chassis and a contacting relation with a wearer's body in use; and
  c) a dewatering layer formed from a material separate from said containment flap and also joined on an outer surface of each of said containment flaps for absorbing at least a portion of any exudates which pass between said distal edge and said wearer's body in use.

21. An absorbent article according to claim 20 wherein said proximal edge of each of said containment flaps is attached to said topsheet layer of said absorbent chassis.

22. An absorbent article according to claim 20 wherein said dewatering layer defines a length which is less than about 75 percent of a length of said containment flap.

23. An absorbent article according to claim 20 wherein said dewatering layer defines a width which is less than about 75 percent of a width of said containment flap.

24. An absorbent article according to claim 20 wherein said dewatering layer defines an absorbency of at least about 3 grams of saline solution per gram.

25. An absorbent article according to claim 20 wherein said dewatering layer defines a basis weight of at least about 30 grams per square meter.

* * * * *